United States Patent [19]

Hübele et al.

[11] 4,330,556
[45] May 18, 1982

[54] MICROBICIDAL N-1'-HYDROCARBYLOXYCARBONYLETHYL)-N-ALKOXYACETYLANILINES

[75] Inventors: Adolf Hübele, Magden, Switzerland; Wolfgang Eckhardt, Lörrach, Fed. Rep. of Germany; Walter Kunz, Oberwil, Switzerland

[73] Assignee: Ciba-Geigy Corporation, Ardsley, N.Y.

[21] Appl. No.: 222,406

[22] Filed: Jan. 5, 1981

Related U.S. Application Data

[63] Continuation of Ser. No. 86,008, Oct. 17, 1979, abandoned.

[30] Foreign Application Priority Data

Oct. 27, 1978 [CH] Switzerland ............... 11119/78

[51] Int. Cl.³ ............... C07C 101/447; A01N 37/22; A01N 37/24
[52] U.S. Cl. ............... 424/309; 424/303; 424/285; 424/304; 260/456 A; 260/465 D; 560/15; 560/34; 560/43; 549/487
[58] Field of Search ............... 560/9, 34, 43; 260/456 A, 465 D; 424/303, 304, 309

[56] References Cited

U.S. PATENT DOCUMENTS

| | | | |
|---|---|---|---|
| 4,046,911 | 9/1977 | Hubele | 260/347.4 |
| 4,094,990 | 6/1978 | Hubele | 424/285 |
| 4,143,155 | 3/1979 | Hubele et al. | 424/303 |
| 4,151,299 | 4/1979 | Hubele et al. | 424/309 |
| 4,207,338 | 6/1980 | Eckhardt et al. | 560/34 |

FOREIGN PATENT DOCUMENTS

2311897 4/1973 Fed. Rep. of Germany.
2648074 4/1978 Fed. Rep. of Germany.

OTHER PUBLICATIONS

Hubele, Chem. Absts., 84, 30713(m), 58964(t), 1976.
Hubele et al., Chem. Absts., 84, 17120(w), 1976.
Hubele et al., Chem. Absts., 89, 23995(e), 1978.

*Primary Examiner*—G. T. Breitenstein
*Attorney, Agent, or Firm*—Frederick H. Rabin

[57] ABSTRACT

Compounds of the formula

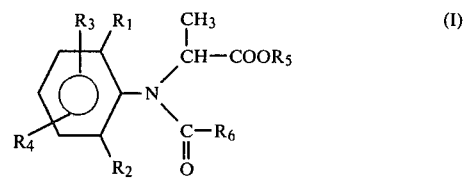

wherein
$R_1$ and $R_2$ independently of one another are each $C_1$–$C_3$-alkyl, $C_1$–$C_3$-alkoxy or halogen,
$R_3$ is hydrogen, $C_1$–$C_3$-alkyl or halogen,
$R_4$ is hydrogen or methyl, the total number of carbon atoms in $R_1$, $R_2$, $R_3$ and $R_4$ not exceeding 6,
$R_5$ is $C_3$–$C_8$-alkyl, $C_2$–$C_6$-alkenyl or $C_3$–$C_6$-alkynyl both unsubstituted or substituted by halogen, or it is $C_3$–$C_7$-cycloalkyl unsubstituted or substituted by halogen or $C_1$–$C_3$-alkyl, or it is $C_6$–$C_{10}$-aryl unsubstituted or substituted by halogen, cyano, nitro, $C_1$–$C_3$-alkyl, $C_1$–$C_3$-alkoxy or $C_1$–$C_2$-halogenoalkyl,
$R_6$ is 2-furyl or 2-tetrahydrofuryl both unsubstituted or substituted by halogen, or $R_6$ is $\beta$-($C_1$–$C_4$)-alkoxyethyl, or the group $CH_2Z$, where Z is one of the groups (a) -X-$R_7$, (b) -NH-N($R_8$)($R_9$), (c) -OSO$_2$$R_{10}$ and (d)

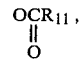

wherein
X is oxygen or sulfur, $R_7$ is $C_1$–$C_6$-alkyl which is unsubstituted or substituted by $C_1$–$C_2$-alkoxy, or it is $C_3$–$C_4$-alkenyl or $C_3$–$C_4$-alkynyl, $R_8$ is hydrogen or $C_1$–$C_3$-alkyl, $R_9$ is $C_1$–$C_3$-alkyl, or phenyl which is unsubstituted or substituted by halogen or by methyl, $R_{10}$ is $C_1$–$C_4$-alkyl or mono- or di-($C_1$–$C_3$)-alkylamine, and $R_{11}$ is $C_1$–$C_3$-alkyl which is unsubstituted or substituted by $C_1$–$C_2$-alkoxy constitute valuable microbicides. They can be applied, together with customary carriers and formulation additives, in the form of preparations to combat in particular phytopathogenic fungi.

6 Claims, No Drawings

MICROBICIDAL N-1'-HYDROCARBYLOXYCARBONYLETHYL)-N-ALKOXYACETYLANILINES

This is a continuation of application Ser. No. 86,008 filed on Oct. 17, 1979, now abandoned.

The present invention relates to compounds of the formula I (I) [structure: benzene ring with substituents $R_3$, $R_1$ (top), $R_4$, $R_2$ (bottom), and N attached to $CH(CH_3)$—$COOR_5$ and $C(=O)$—$R_6$]

wherein
$R_1$ and $R_2$ independently of one another are each $C_1$–$C_3$-alkyl, $C_1$–$C_3$-alkoxy or halogen,
$R_3$ is hydrogen, $C_1$–$C_3$-alkyl or halogen,
$R_4$ is hydrogen or methyl, the total number of carbon atoms in $R_1$, $R_2$, $R_3$ and $R_4$ not exceeding 6,
$R_5$ is $C_3$–$C_8$-alkyl, $C_2$–$C_6$-alkenyl or $C_3$–$C_6$-alkynyl both unsubstituted or substituted by halogen, or it is $C_3$–$C_7$-cycloalkyl unsubstituted or substituted by halogen or $C_1$–$C_3$-alkyl, or it is $C_6$–$C_{10}$-aryl unsubstituted or substituted by halogen, cyano, nitro, $C_1$–$C_3$-alkyl, $C_1$–$C_3$-alkoxy or $C_1$–$C_2$-halogenoalkyl,
$R_6$ is 2-furyl or 2-tetrahydrofuryl both unsubstituted or substituted by halogen, or $R_6$ is $\beta$-($C_1$–$C_4$)-alkoxyethyl, or the group $CH_2Z$, where Z is one of the groups (a) —X—$R_7$, (b) —NH—N($R_8$)($R_9$), (c) —$OSO_2R_{10}$ and (d)

$$-O-C(=O)-R_{11}$$

wherein
X is oxygen or sulfur, $R_7$ is $C_1$–$C_6$-alkyl which is unsubstituted or substituted by $C_1$–$C_2$-alkoxy, or it is $C_3$–$C_4$-alkenyl or $C_3$–$C_4$-alkynyl, $R_8$ is hydrogen or $C_1$–$C_3$-alkyl, $R_9$ is $C_1$–$C_3$-alkyl, or phenyl which is unsubstituted or substituted by halogen or by methyl, $R_{10}$ is $C_1$–$C_4$-alkyl or mono- or di-($C_1$–$C_3$)-alkylamine, and $R_{11}$ is $C_1$–$C_3$-alkyl which is unsubstituted or substituted by $C_1$–$C_2$-alkoxy.

By alkyl or by alkyl part of another substituent are meant, depending on the given number of C atoms, the following groups: methyl, ethyl, propyl, butyl, pentyl, hexyl, heptyl or octyl, and also isomers thereof, for example iso-propyl, iso-butyl, sec-butyl, tert-butyl, iso-pentyl, and so forth.

Alkenyl is for example allyl, 2-butenyl, 3-pentenyl, etc.

Alkynyl denotes in particular propargyl.

As $C_3$–$C_7$-cycloalkyl are meant cyclopropyl, cyclobutyl, cyclopentyl, cyclohexyl and cycloheptyl.

By aryl is meant in particular phenyl and naphthyl.

Halogen is fluorine, chlorine, bromine or iodine.

The compounds of the formula I can be produced by a whole series of methods, such as by those described in the following. In the formulae II to XXII, the symbols $R_1$ to $R_{11}$ and X have the meanings given under the formula I, "Hal" denotes halogen, preferably chlorine or bromine, and M is hydrogen or a metal cation, preferably an alkali metal cation or alkaline-earth metal cation.

A. [scheme: aniline (II) with $R_1$–$R_4$ and NHCH(CH_3)COOR_5$ + HOOCR_6$ (III) $\xrightarrow{\text{acylation}}$ (I)]

There can preferably be used here a reactive derivative of a compound of the formula III, for example the acid halide, acid anhydride or the ester. Method A may be modified by starting with compound II wherein $R_5$ represents hydrogen which method results in compound XVI hereunder, with subsequent esterification by method G.

In some cases, the use of acid-binding agents and/or condensation agents is advantageous. Suitable as such are for example: tertiary amines such as trialkylamines (for example triethylamine), pyridine or pyridine bases, or inorganic bases, such as the oxides, hydroxides, hydrogen carbonates, carbonates or hydrides of alkali metals and alkaline-earth metals, and also sodium acetate. The starting product II can moreover serve as acid-binding agent, and should be used in excess.

The production process A can also be performed without an acid-binding agent. In some cases the passing through of nitrogen to expel the hydrogen halide formed is advisable. In other cases, an addition of dimethylformamide as reaction catalyst is very advantageous.

B. When $R_6$ is —$CH_2OSO_2R_{10}$ or —$CH_2O(CO)R_{11}$

[scheme: compound (IV) with CHCOOR_5$ and C(=O)—$CH_2OH$ + Hal-$SO_2R_{10}$ (V) or Hal-$CR_{11}$(=O) (VI) $\longrightarrow$ (I)]

There is advantageously used a salt, especially an alkali metal salt, of the compound of the formula IV. This process can be carried out, as described under A, in the presence of an acid-binding agent.

C. When $R_6$ has a meaning other than —$CH_2NH$—N($R_8$)($R_9$):

[scheme: anilide (VII) NH—C(=O)—$R_6$ + HalCH(CH_3)COOR_5$ (VIII) $\longrightarrow$ (I)]

In this case, the compound of the formula VII is firstly converted with butyl-lithium or sodium hydride into the corresponding alkali metal salt, or alternatively the process is performed in the presence of an acid-binding agent, analogously to process A, preferably with the addition of catalytic amounts of alkali iodide.

D. When $R_6$ is —$CH_2XR_7$, —$CH_2O(CO)R_{11}$ or —$CH_2NH$—$N(R_8)(R_9)$:

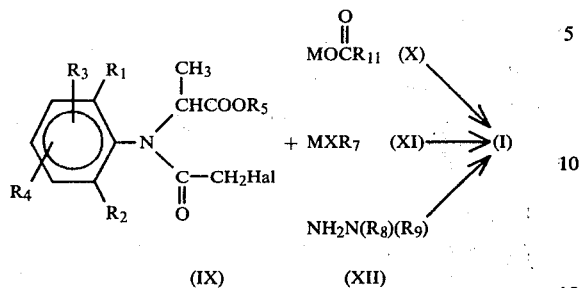

If M is hydrogen, the presence of a salt-forming agent is advantageous, for example the oxide, hydroxide or hydride of an alkali metal or alkaline-earth metal. Where starting materials of the formula XII are used, the final product is obtained as hydrogen halide. With mild bases, it is possible to obtain at room temperature or at slightly elevated temperature the free hydrazino compound. Suitable for this are for example alkali carbonates.

E. When $R_6$ is $\beta$-($C_1$-$C_4$)-alkoxyethyl:

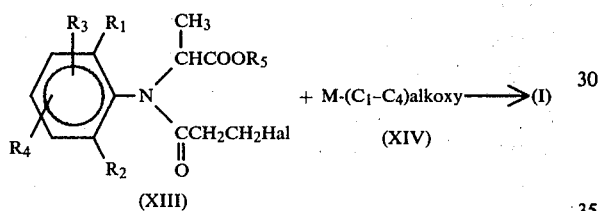

The procedure in this case is analogous to that for process D.

F. When $R_6$ is $\beta$-($C_1$-$C_4$)-alkoxyethyl:

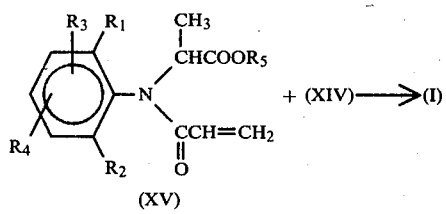

In this process there is carried out with the alcohol or with the alcoholate XIV (M=metal atom) a Michael addition.

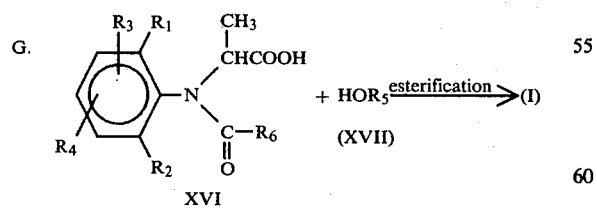

There is advantageously used in this process an esterification catalyst, for example mineral acids, chlorosulfonic acid, toluenesulfonic acid, acid chlorides such as thionyl chloride, acetyl chloride, phosphorus oxychloride, oxalyl chloride, boron trifluoride etherate, and so forth. It is also possible to carry out the reaction with an excess of $HOR_5$. The azeotropic esterification method is advantageous in many cases.

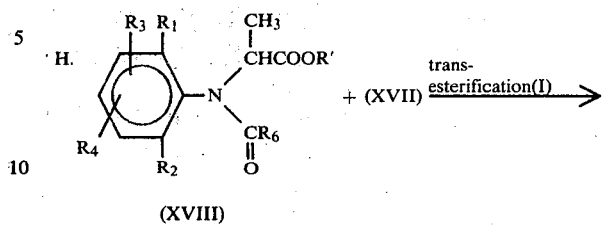

This reaction is catalytically influenced by acids and bases. In order to displace the equilibrium as far as possible in the desired direction, the reaction is performed with an excess of $HOR_5$. The meanings of R' and $R_5$ are different. R' is preferably lower alkyl, such as methyl or ethyl.

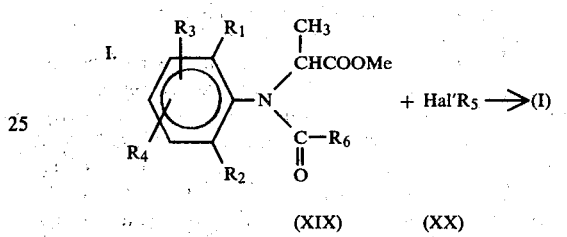

In this case, Me denotes an alkali metal, alkaline-earth metal, lead or silver atom, Hal' is halogen, preferably chlorine, bromine or iodine.

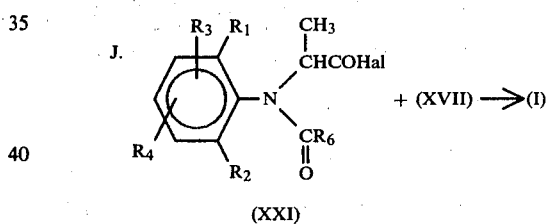

This reaction can if required be performed with an acid-binding agent.

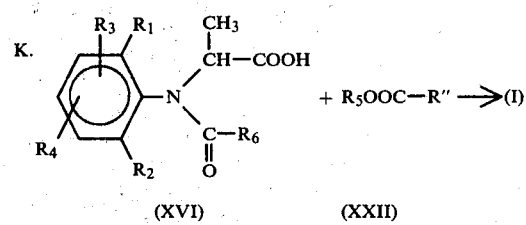

R" is here lower alkyl, preferably methyl.

In all processes, there may be used solvents which are inert to the reactants. Examples of such solvents are: aliphatic hydrocarbons, such as benzene, toluene, xylenes or petroleum ether; halogenated hydrocarbons, such as chlorobenzene, methylene chloride, ethylene chloride or chloroform; ethers and ethereal compounds, such as dialkyl ether, dioxane and tetrahydrofuran; nitriles, such as acetonitrile; N,N-dialkylated amides, such as dimethylformamide; dimethyl sulfoxide, ketones, such as methyl ethyl ketone; and mixtures of solvents of this type.

All starting materials are produced by methods known per se (see J. Org. Chem., 30, 4101 (1965); Tetrahedron 1967, 487; Tetrahedron, 1967, 493; German Offenlegungsschrift No. 2,417,781; German Offenlegungsschrift No. 2,311,897; U.S. Pat. No. 3,780,090; U.S. Pat. No. 3,598,859; and Great Britain Pat. Specification No. 1,438,311).

The various processes likewise form subject matter of the present invention.

The compounds of the formula I have, in a position adjacent to COOR$_5$, an asymmetrical carbon atom in the side chain, and can be split in the customary manner into optical antipodes (fractional crystallisation or column chromatography either with compounds of the formula I or with the intermediate products, and further reaction of the resolved antipodes). The antipodes I have a varying microbicidal action.

Further asymmetrical carbon atoms can be present in the molecule, depending on substitution.

Independently of the stated optical isomerism, there is observed as a rule an atropisomerism around the

axis in those cases where the phenyl ring is substituted at least in the 2,6-position and simultaneously unsymetrically with respect to this axis (optionally therefore also as a result of the presence of additional substituents).

If no specific synthesis is carried out to isolate pure isomers, there is normally obtained a product of the formula I as a mixture of these possible isomers.

The compounds of the formula I can be used on their own or together with suitable carriers and/or other additives. Suitable carriers and additives can be solid or liquid and they correspond to the substances common in formulation practice, such as natural or regenerated mineral substances, solvents, dispersing agents, wetting agents, adhesives, thickeners, binders and/or fertilisers. Dispersing agents and wetting agents belong to the surface-active additives.

The content of active substance in commercial compositions is between 0.1 and 90%.

The compounds of the formula I can be in the following forms for application (the weight-percentage figures in brackets signify advantageous amounts of active substance):
solid preparations:
  dusts and scattering agents (up to 10%), and granulates [coated granules, impregnated granules and homogeneous granules] (1 to 80%);
liquid preparations:
  (a) water-dispersible concentrates of active substance: wettable powders and pastes (25 to 90% in the commercial packing, 0.01 to 15% in ready-for-use solutions); emulsion concentrates and solution concentrates (10 to 50%; 0.01 to 15% in ready-for-use solutions);
  (b) solutions (0.1 to 20%) and aerosols.

Compositions of this type likewise form subject matter of the present invention.

It has now been found that compounds having the structure of the formula I surprisingly exhibit a very favourable microbicidal spectrum for practical requirements for the protection of cultivated plants. Cultivated plants within the scope of the present invention are for example: cereals, maize, rice, vegetables, sugar beet, soya bean, groundnuts, fruit trees or ornamental plants, especially however grape vines, hops, cucurbitaceae (cucumbers, pumpkins, melons), solanaceae, such as potatoes, tobacco and tomatoes, and also bananas, cocoa and natural rubber plants.

Fungi occurring on plants or on parts of plants (fruit, blossom, foliage, stalks, tubers or roots) of the said crops and of related cultivated crops can be inhibited or destroyed with the active substances of the formula I, and also parts of plants subsequently growing remain preserved from such fungi. The active substances are effective against the phytopathogenic fungi belonging to the following classes: Ascomycetes (for example Erysiphaceae, Sclerotinia, Helminthosporium); Basidiomycetes, such as in particular rust fungi, Rhizoctonia; fungi imperfecti (for example Moniliales, Piricularia); and especially against the Oomycetes belonging to the Phycomycetes class, such as Phytophthora, Peronospora, Pseudoperonospora, Pythium or Plasmopara. Furthermore, the compounds of the formula I have a systemic action. They can also be used as dressing agents for the treatment of seed (fruits, tubers, grain, etc.) and plant cuttings to protect them from fungus infections, and also against phytopathogenic fungi occurring in the soil.

The invention hence relates also to the use of the compounds of the formula I for controlling phytopathogenic microorganisms.

The following group is preferred:
R$_1$ is C$_1$–C$_2$-alkyl or C$_1$–C$_2$-alkoxy,
R$_2$ is CH$_3$, —OCH$_3$ or halogen,
R$_3$ is hydrogen, CH$_3$ or halogen,
R$_4$ is hydrogen or CH$_3$,
R$_5$ is C$_3$–C$_6$-alkyl or C$_2$–C$_4$-alkenyl, C$_3$–C$_4$-alkynyl or C$_3$–C$_7$-cycloalkyl,
R$_6$ is 2-furyl, 2-tetrahydrofuryl, β-(C$_1$–C$_2$-alkoxy)-ethyl or CH$_2$Z, the meaning of Z being —OR$_7$, —SR$_7$, —NH—N(R$_8$)(R$_9$) or —OSO$_2$R$_{10}$, wherein R$_7$ is C$_1$–C$_4$-alkyl which is unsubstituted or substituted by C$_1$–C$_2$-alkoxy, or it is C$_3$–C$_4$-alkenyl or C$_3$–C$_4$-alkynyl, R$_8$ and R$_9$ independently of one another are each C$_1$–C$_3$-alkyl, and R$_{10}$ is C$_1$–C$_2$-alkyl or monomethylamine.

The following subgroup is particularly preferred:
R$_1$ is CH$_3$ or OCH$_3$,
R$_2$ is CH$_3$ or chlorine,
R$_3$ is hydrogen,
R$_4$ is hydrogen,
R$_5$ is C$_3$–C$_4$-alkyl, C$_3$-alkenyl or C$_3$-alkynyl,
R$_6$ is 2-furyl, 2-tetrahydrofuryl, CH$_2$CH$_2$OCH$_3$ or CH$_2$Z, the meaning of Z being —OR$_7$, —NH—N(R$_8$)(R$_9$) or —OSO$_2$R$_{10}$, wherein R$_7$ is C$_1$–C$_3$-alkyl, R$_8$ and R$_9$ independently of one another are each C$_1$–C$_2$-alkyl, and R$_{10}$ is C$_1$–C$_2$-alkyl or monomethylamine.

The following Examples serve to further illustrate the invention without limiting the scope thereof. The temperature values are given in degrees Centigrade, and percentages and parts relate to weight. Except where otherwise stated, the term 'active substance of the formula I' denotes always the racemic mixture.

Production Example

Production of N-(1'-isopropoxycarbonyl-ethyl)-N-methoxyacetyl-2,6-dimethylaniline of the formula

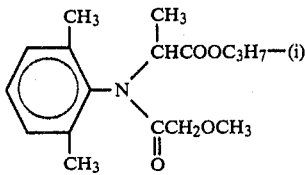

26.5 g of N-(1'-carboxyethyl)-N-methoxyacetyl-2,6-dimethylaniline, 30 g of isopropanol and 2 g of conc. sulfuric acid were refluxed for 20 hours; isopropanol was then evaporated off, 200 ml of water was added to the residue, and extraction was performed with 100 ml of diethyl ether each time. The combined extracts were washed with a little water, dried over sodium sulfate and filtered, and the solvent was evaporated off. The crude product was distilled under high vacuum; b.p. 145°/0.04 mbar. The compound of the formula I thus produced is particularly preferred as being one of the most effective compounds of the formula I.

The following compounds of the formula I can be produced in an analogous manner or by one of the methods given in the foregoing ($R_1$=2-position, $R_2$=6-position).

| Comp. No. | $R_1$ | $R_2$ | $R_3$ | $R_4$ | $R_5$ | $R_6$ | Physical constants |
|---|---|---|---|---|---|---|---|
| 1 | $CH_3$ | $CH_3$ | H | H | —$C_3H_7$—i | —$CH_2OCH_3$ | b.p.145°/0,04 mbar |
| 2 | $CH_3$ | $CH_3$ | H | H | —$C_3H_7$—i | furanyl | b.p. 140-145°/0,027 mbar |
| 3 | $CH_3$ | $CH_3$ | H | H | —$CH_2$—CH=$CH_2$ | —$CH_2OCH_3$ | b.p. 56-59° |
| 4 | $CH_3$ | $CH_3$ | H | H | —$C_3H_7$—n | —$CH_2OCH_3$ | b.p. 67-69° |
| 5 | $CH_3$ | $CH_3$ | H | H | —$C_4H_9$—n | —$CH_2OCH_3$ | b.p. 25,5-27° |
| 6 | $CH_3$ | $CH_3$ | 3-$CH_3$ | 5-$CH_3$ | —$C_3H_7$—n | —$CH_2OCH_3$ | b.p. 87-90° |
| 7 | $CH_3$ | $CH_3$ | H | H | —$C_4H_9$sek. | furanyl | |
| 8 | $CH_3$ | $CH_3$ | H | H | —$C_4H_9$sek. | —$CH_2OCH_3$ | b.p. 126-127°/0.05mbar |
| 9 | $CH_3$ | $CH_3$ | H | H | —$CH_2$—C≡CH | —$CH_2OCH_3$ | b.p. 88-90° |
| 10 | $CH_3$ | $CH_3$ | H | H | —$C_3H_7$—i | —$CH_2OSO_2NHCH_3$ | |
| 11 | $CH_3$ | $CH_3$ | H | H | —$C_8H_{17}$—n | —$CH_2OCH_3$ | |
| 12 | $CH_3$ | $CH_3$ | 3-$CH_3$ | 5-$CH_3$ | —$C_3H_7$—i | —$CH_2OC_2H_5$ | |
| 13 | $CH_3$ | $CH_3$ | H | H | cyclohexyl | —$CH_2OCH_3$ | b.p.73,5-75,5° |
| 14 | $CH_3$ | $CH_3$ | 3-$CH_3$ | 5-$CH_3$ | —$C_3H_7$—n | —$CH_2OC_2H_5$ | |
| 15 | $CH_3$ | Cl | H | H | —$C_3H_7$—i | —$CH_2OCH_3$ | b.p.158°/0,03 mbar |
| 16 | $CH_3$ | $OCH_3$ | H | H | —$C_3H_7$—i | furanyl | |
| 17 | $CH_3$ | $CH_3$ | H | H | —CH=$CH_2$ | —$CH_2OCH_3$ | |
| 18 | $CH_3$ | $OCH_3$ | H | H | —$C_3H_7$—i | —$CH_2OCH_3$ | b.p.161°/0,04 mbar |
| 19 | $CH_3$ | $CH_3$ | H | H | phenyl | —$CH_2OCH_3$ | brown oil |
| 20 | $CH_3$ | $CH_3$ | H | H | —$C_3H_7$—n | —$CH_2OSO_2C_2H_5$ | |
| 21 | $CH_3$ | $C_2H_5$ | H | H | —$C_3H_7$—i | —$CH_2OCH_3$ | |
| 22 | $CH_3$ | $CH_3$ | H | H | cyclohexyl | furanyl | |
| 23 | $CH_3$ | $CH_3$ | H | H | —$C_3H_7$—n | —$CH_2OSO_2NHCH_3$ | |
| 24 | $CH_3$ | $CH_3$ | 3-$CH_3$ | H | —$C_3H_7$—i | —$CH_2OCH_3$ | b.p. 148°/0,04 mbar |
| 25 | $CH_3$ | $CH_3$ | H | H | —$C_3H_7$—i | —$CH_2OSO_2C_2H_5$ | |
| 26 | $CH_3$ | $CH_3$ | H | H | —$C_3H_7$—i | —$CH_2OSO_2CH_3$ | |
| 27 | $CH_3$ | $C_2H_5$ | H | H | —$C_3H_7$—n | —$CH_2OCH_3$ | |
| 28 | $CH_3$ | $CH_3$ | H | H | —$C_3H_7$—i | bromofuranyl | |
| 29 | $CH_3$ | $CH_3$ | H | H | —$C_3H_7$—n | —$CH_2OSO_2CH_3$ | |
| 30 | $CH_3$ | $CH_3$ | H | H | —$C_3H_7$—i | tetrahydrofuranyl | |

-continued

| Comp. No. | R₁ | R₂ | R₃ | R₄ | R₅ | R₆ | Physical constants |
|---|---|---|---|---|---|---|---|
| 31 | CH₃ | CH₃ | H | H | —C₃H₇—i | —CH₂NH—N(CH₃)₂ | |
| 32 | CH₃ | CH₃ | 3-CH₃ | H | —C₃H₇—n | —CH₂OCH₃ | |
| 33 | CH₃ | CH₃ | H | H | —C₃H₇—n | —CH₂NH—N(CH₃)₂ | |
| 34 | CH₃ | CH₃ | 3-CH₃ | H | —CH₂—CH=CH₂ | —CH₂OCH₃ | |
| 35 | CH₃ | CH₃ | 3-Cl | H | —CH₂CH=CH₂ | —CH₂OCH₃ | |
| 36 | CH₃ | CH₃ | H | H | —C₃H₇—n | tetrahydrofuranyl | |
| 37 | CH₃ | CH₃ | 3-CH₃ | 5-CH₃ | —C₃H₇—i | tetrahydrofuranyl | b.p. 153°/0,03 mbar |
| 38 | CH₃ | CH₃ | H | H | —C₃H₇—i | —CH₂SCH₃ | b.p. 45-49° |
| 39 | CH₃ | CH₃ | H | H | —C₃H₇—i | —CH₂CH₂OCH₃ | |
| 40 | CH₃ | CH₃ | 3-CH₃ | H | —C₃H₇—i | —CH₂OC₂H₅ | b.p. 157°/0,03 mbar |
| 41 | CH₃ | CH₃ | H | H | —C₃H₇—i | —CH₂OC₂H₅ | b.p. 154°/0,03 mbar |
| 42 | CH₃ | CH₃ | H | H | —C₃H₇—i | —CH₂OCCH₃‖O | b.p. 144-145°/0,0013 mbar |
| 43 | CH₃ | CH₃ | H | H | —C₃H₇—i | —CH₂NH—NH—cyclohexyl | |
| 44 | CH₃ | CH₃ | H | H | —C₃H₇—i | —CH₂OCH₂C≡CH | |
| 45 | CH₃ | CH₃ | 3-Cl | H | —C₃H₇—i | —CH₂OC₂H₅ | b.p. 160°/0,04 mbar |
| 46 | CH₃ | CH₃ | H | H | —C₃H₇—n | —CH₂OC₂H₅ | |
| 47 | CH₃ | CH₃ | 3-CH₃ | H | —C₃H₇—i | tetrahydrofuranyl | |
| 48 | CH₃ | CH₃ | H | H | —CH₂—CH=CH₂ | —CH₂OC₂H₅ | |
| 49 | CH₃ | CH₃ | 3-CH₃ | 5-CH₃ | —C₃H₇—n | tetrahydrofuranyl | |
| 50 | CH₃ | CH₃ | H | H | —C₃H₇—n | —CH₂OCH₂—CH=CH₂ | |
| 51 | CH₃ | CH₃ | 3-CH₃ | H | —C₃H₇—n | tetrahydrofuranyl | |
| 52 | CH₃ | CH₃ | 3-Cl | H | —CH₂—C≡CH | —CH₂OCH₃ | |
| 53 | CH₃ | CH₃ | 3-CH₃ | 5-CH₃ | —CH₂CH=CH₂ | —CH₂OCH₃ | |
| 54 | CH₃ | CH₃ | H | H | —C₆H₄—Cl | —CH₂OCH₃ | |
| 55 | CH₃ | CH₃ | 3-CH₃ | 5-CH₃ | —CH₂—C≡CH | —CH₂OCH₃ | |
| 56 | CH₃ | CH₃ | H | H | —C₃H₇—i | —CH₂OC₃H₇—i | |
| 57 | CH₃ | CH₃ | 3-Cl | H | —C₃H₇—i | tetrahydrofuranyl | |
| 58 | CH₃ | CH₃ | 3-CH₃ | 5-CH₃ | —C₃H₇—i | —CH₂OCH₃ | b.p. 162°/0,035mbar |
| 59 | CH₃ | CH₃ | H | H | β-naphthyl | —CH₂OCH₃ | |
| 60 | CH₃ | CH₃ | H | H | —C₃H₇—i | —CH₂OCH₂CH=CH₂ | |
| 61 | CH₃ | CH₃ | 3-Cl | H | —C₃H₇—i | —CH₂OCH₃ | b.p. 170°/0,04mbar light-brown oil |
| 62 | CH₃ | CH₃ | H | H | —CH(CH₃)CH₂CH₂CH₃ | —CH₂OCH₃ | |
| 63 | CH₃ | CH₃ | H | H | —C₃H₇—i | —CH₂SC₂H₅ | Smp. 63-64,5° |
| 64 | CH₃ | CH₃ | H | H | —C₃H₇—i | —CH₂SC₃H₇—i | light-brown oil |

Formulation Examples

Wettable powder:

The following constituents are used to produce (a) a 40% wettable powder and (b) a 10% wettable powder:

(a)

40 parts of active substance, 5 parts of sodium lignin sulfonate,
1 part of sodium dibutylnaphthalenesulfonate, and
54 parts of silicic acid; and
(b)
10 parts of active substance,
3 parts of a mixture of the sodium salts of saturated fatty alcohol sulfates,
5 parts of naphthalenesulfonic acid/formaldehyde condensate, and
82 parts of kaolin.

The active substances are intimately mixed in suitable mixers with the additives, and the mixture is then ground in the appropriate mills and rollers. There are obtained wettable powders which have excellent wetting and suspension properties, and which can be diluted with water to give suspensions of the desired concentration, and these are particularly suitable for leaf application.

Emulsifiable concentrate:
The following substances are used to produce a 25% emulsifiable concentrate:
25 parts of active substance,
2.5 parts of epoxidised vegetable oil,
10 parts of an alkylarylsulfonate/fatty alcohol polyglycol ether mixture,
5 parts of dimethylformamide, and
57.5 parts of xylene.

Emulsions of the desired concentration can be prepared from these concentrates by dilution with water, and they are particularly suitable for leaf application.

BIOLOGICAL EXAMPLES

EXAMPLE 1

Action against Phytophthora on tomato plants (a) Residual protective action

Tomato plants after three-weeks' cultivation were sprayed with a spray liquor prepared from wettable powder of the active substance (0.06% of active substance). The treated plants were infested after 24 hours with a suspension of sporangia of the fungus. An assessment of the fungus infection was made after incubation of the infested plants during 5 days at 90–100% relative humidity at 20° C.

(b) Residual curative action

Tomato plants were infested, after a cultivation period of three weeks, with a suspension of sporangia of the fungus. After an incubation time of 22 hours in a moist chamber at 20° C. with 90–100% relative humidity, the infested plants were dried, and then sprayed with a spray liquor prepared from wettable powder of the active substance (0.06% of active substance). After drying of the applied coating, the treated plants were returned to the moist chamber. The assessment of fungus infection was carried out 5 days after infestation.

(c) Systemic action

A spray liquor prepared from wettable powder of the active substance (0.006% of active substance, relative to the volume of soil) was applied to the soil in which tomato plants had been cultivated for 3 weeks. Care was taken to ensure that the spray liquor did not come into contact with the parts of the plants above the soil. After 48 hours, the treated plants were infested with a suspension of sporangia of the fungus. An assessment of fungus infection was made after incubation of the infested plants during 5 days at 20° C. with 90–100% relative humidity.

Compared with the fungus infection occurring on the control plants, the infection on plants treated with the compounds Nos. 1, 3, 4, 5, 6, 9, 15, 24, 31, 58, 61 and 62 and with other compounds according to the invention was almost completely prevented (0–5% infection).

EXAMPLE 2

Action against Plasmopara viticola on grape vines

Grape-vine cuttings in the 4-5-leaf stage were sprayed with a spray liquor prepared from wettable powder of the active substance (0.06% of active substance). After 24 hours, the treated plants were infested with a suspension of sporangia of the fungus. The extent of fungus infection was assessed after incubation during 6 days at 20° C. with 95–100% relative humidity.

Compared with the fungus infection present on the infested control plants, the infection on plants after treatment with the compounds Nos. 1, 3, 4, 5, 6, 9, 15, 24, 31, 58, 61 and 62 and with other compounds according to the invention was almost completely inhibited (0–5% infection).

EXAMPLE 3

Action against Pythium debaryanum on carrots

Action after soil application

The fungus was cultivated on a carrot-chips nutrient solution, and applied to a soil/sand mixture. The soil infested in this manner was placed into flower pots, and sown with sugar-beet seeds. Immediately after sowing, the test preparations, formulated as wettable powder, were poured as aqueous suspensions over the soil (20 ppm of active substance, relative to the volume of soil). The pots were subsequently left for 2-3 weeks in a greenhouse at about 20° C. The soil was continuously maintained uniformly moist by light spraying.

In the evaluation of the test results, the sprouting of the sugar-beet plants and also the proportion of healthy plants and diseased plants were determined.

Action after dressing application

The fungus was cultivated on a carrot-chips nutrient solution, and applied to a soil/sand mixture. The soil infested in this manner was placed into soil trays, and sown with sugar-beet seeds which had been dressed with the test preparations formulated as dressing powder (0.06% of active substance). The sown trays were left for 2-3 weeks in a greenhouse at about 20° C. The soil was continuously maintained uniformly moist by light spraying. In the final evaluation, the sprouting of the plants was assessed.

Both after soil application and after dressing application with the compounds Nos. 1, 2, 3, 4, 5, 6, 10, 12, 15, 18, 24, 30, 37, 40, 41, 45, 58, 61 and 62 and with other compounds according to the invention, over 80% of the plants emerged and had a healthy appearance.

EXAMPLE 4

Residual protective action against Erysiphe graminis on barley plants

Barley plants about 8 cm high were sprayed with a liquor prepared from wettable powder of the active substance No. 64 (containing 0.006% of active substance). After 4 hours, the treated plants were dusted with conidiospores of the fungus. The infested barley plants were kept in a greenhouse at about 22° C. Whereas the control plants after 10 days were displaying clear symptoms of disease, the plants treated with the active substance No. 64 were free from infection.

What is claimed is:

1. A compound of the formula

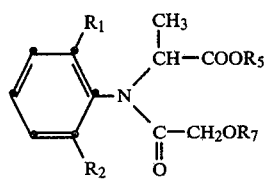

wherein
$R_1$ is methyl or methoxy,
$R_2$ is methyl or chlorine,
$R_5$ is $C_3$ or $C_4$ alkyl, $C_3$ alkenyl or $C_3$ alkynyl, and
$R_7$ is $C_1$–$C_3$ alkyl.

2. N-(1'-Isopropoxycarbonyl-ethyl)-N-methoxyacetyl-2,6-dimethylaniline according to claim 1.

3. A microbicidal composition containing as active substance a compound according to claim 1, together with a suitable carrier and/or a surface-active additive.

4. A composition according to claim 3, containing as active substance N-(1'-isopropoxycarbonyl-ethyl)-N-methoxyacetyl-2,6-dimethylaniline.

5. A method for combatting phytopathogenic fungi which comprises applying thereto a fungicidally effective amount of a compound according to claim 1.

6. The method of combatting phytopathogenic fungi which comprises applying thereto a fungicidally effective amount of the compound according to claim 2.

* * * * *